United States Patent
Wehning et al.

(10) Patent No.: US 9,067,360 B2
(45) Date of Patent: Jun. 30, 2015

(54) DEVICE AND METHOD FOR GENERATIVE PRODUCTION

(75) Inventors: Ralf Wehning, Grasberg (DE); Carsten Vagt, Oyten (DE); Ingo Uckelmann, Breman (DE); Sascha Gartner, Breman (DE)

(73) Assignee: BEGO MEDICAL GMBH, Bremen (DE)

( * ) Notice: Subject to any disclaimer, the term of this patent is extended or adjusted under 35 U.S.C. 154(b) by 194 days.

(21) Appl. No.: 13/392,442
(22) PCT Filed: Aug. 25, 2010
(86) PCT No.: PCT/EP2010/062371
§ 371 (c)(1),
(2), (4) Date: May 7, 2012
(87) PCT Pub. No.: WO2011/023714
PCT Pub. Date: Mar. 3, 2011

(65) Prior Publication Data
US 2012/0211155 A1 Aug. 23, 2012

(30) Foreign Application Priority Data
Aug. 25, 2009 (EP) ...................................... 09168566

(51) Int. Cl.
*B32B 37/06* (2006.01)
*B29C 67/00* (2006.01)
(Continued)

(52) U.S. Cl.
CPC ......... *B29C 67/0077* (2013.01); *A61C 13/0013* (2013.01); *A61C 13/0018* (2013.01); *B22F 3/1055* (2013.01); *B22F 2003/1057* (2013.01)

(58) Field of Classification Search
CPC ........ B32B 37/00; B32B 37/06; B32B 37/14; B29C 35/08
USPC ........................................... 156/272.2, 275.5
See application file for complete search history.

(56) References Cited

U.S. PATENT DOCUMENTS

| | | | |
|---|---|---|---|
| 4,759,887 A * | 7/1988 | Geissler et al. | 264/414 |
| 2004/0031780 A1 * | 2/2004 | Hagemeister et al. | 219/121.85 |
| 2007/0235904 A1 * | 10/2007 | Saikin | 264/497 |

FOREIGN PATENT DOCUMENTS

| | | | |
|---|---|---|---|
| DE | 29907262 U1 * | 7/1999 | |
| DE | 29907262 | 8/1999 | |

(Continued)

OTHER PUBLICATIONS

The International Search Report in PCT/EP2010/062371 dated Nov. 19, 2010.
(Continued)

*Primary Examiner* — Daniel McNally
(74) *Attorney, Agent, or Firm* — Kilpatrick Townsend and Stockton LLP

(57) ABSTRACT

The invention relates to a process for producing products having a specific geometry, in particular dental prostheses or auxiliary dental parts, comprising the steps of producing a plurality of products on the surface of a substrate plate by selective curing, in particular by selective sintering or melting, wherein the material is applied in successive layers, one or a plurality of predetermined regions are selectively cured by means of high-energy radiation and joined to one or a plurality of regions of the subjacent layer after each application of a layer, wherein the predetermined regions are predetermined according to a cross-sectional geometry of the product in the respective layer. According to the invention, a substrate plate is provided which is subdivided into a first substrate plate segment and at least one further substrate plate segment that are detachably joined to each other or to a base carrier, a first product is produced on the first substrate plate segment by applying successive layers of material onto the first substrate plate segment and selectively curing predetermined regions of each applied layer of material after it has been applied, and at least one further product is produced on the at least one further substrate plate segment by applying successive layers of material onto the further substrate plate segment and selectively curing predetermined regions of each applied layer of material after it has been applied. The invention also relates to an apparatus for conducting such a process.

13 Claims, 8 Drawing Sheets

Figure 1B:
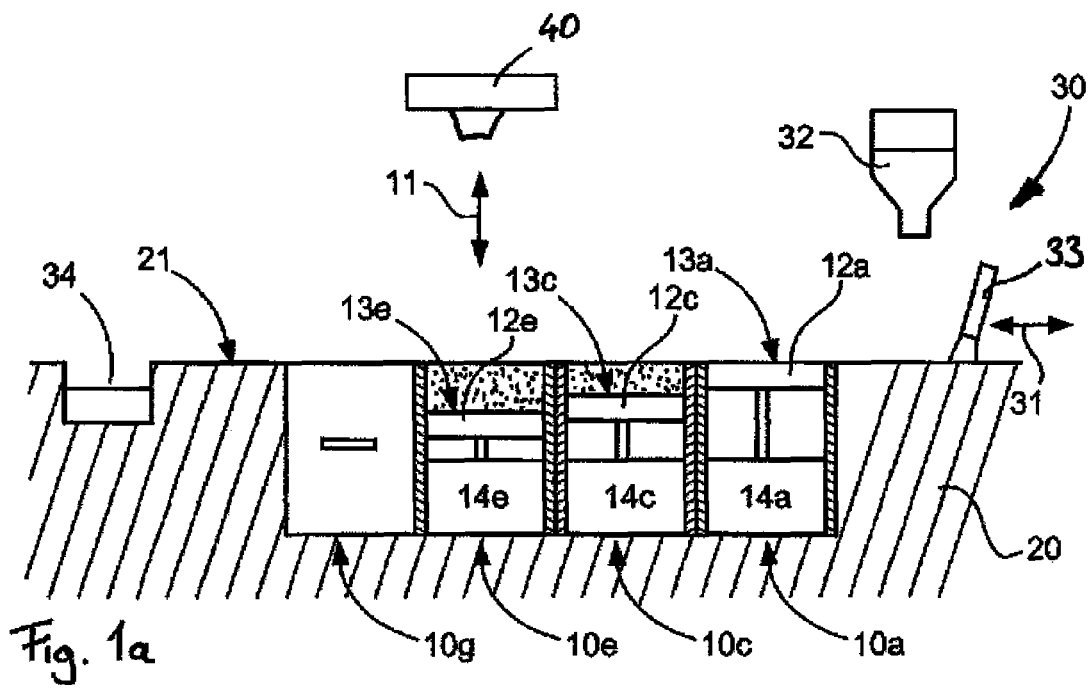
Figure 1B:
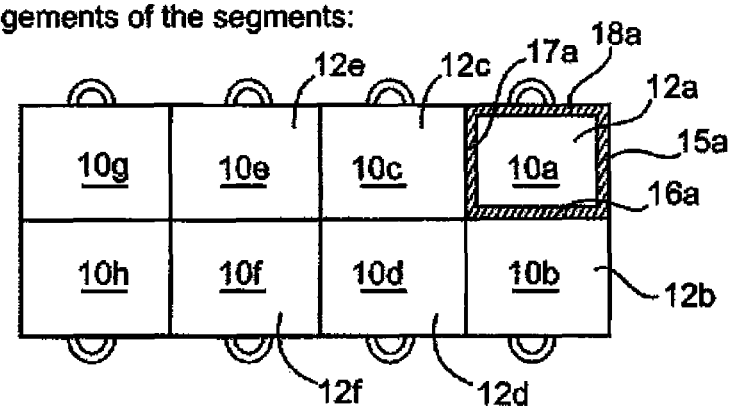

(51) Int. Cl.
*A61C 13/00* (2006.01)
*B22F 3/105* (2006.01)

(56) References Cited

FOREIGN PATENT DOCUMENTS

| DE | 102007047326 | | 4/2009 |
|---|---|---|---|
| DE | 102007047326 A1 | * | 4/2009 |
| EP | 0734842 | | 10/1996 |
| EP | 1021997 | | 7/2000 |
| EP | 2289652 | | 3/2011 |
| WO | WO 2004/014636 | | 2/2004 |
| WO | WO 2008/128502 | | 10/2008 |
| WO | WO 2011/023714 | | 3/2011 |

OTHER PUBLICATIONS

English Translation of Paragraph [0044] of previously cited DE 10 2007 047 326 A1, Herzog, published on Apr. 9, 2009, 1 page.

* cited by examiner

Arrangements of the segments:

DEVICE AND METHOD FOR GENERATIVE PRODUCTION

This application claims priority to and benefit under 35 U.S.C. §119(e) to International Application No. PCT/EP2010/062371 filed Aug. 25, 2010 and to EP Application No. 09168566.9 filed Aug. 25, 2009, the disclosures of which are herein expressly incorporated by reference in their entirety.

The invention relates to a process for producing products having a specific geometry, in particular dental prostheses or auxiliary dental parts, comprising the steps of producing a plurality of products on the surface of a substrate plate by selective curing, in particular by selective sintering or melting, wherein the material is applied in successive layers, one or a plurality of predetermined regions are selectively cured by means of high-energy radiation and joined to one or a plurality of regions of the subjacent layer after each application of a layer, wherein the predetermined regions are predetermined according to a cross-sectional geometry of the product in the respective layer. Another aspect of the invention is an apparatus for conducting such a process.

Generative production processes, i.e., production processes in which a material is shaped in an additive production process to form an individual product, are used in the production of prototypes and meanwhile also in the production of products, in particular in the production of individually shaped products or of products in very small series. Producing individually shaped dental prostheses or auxiliary dental parts by means of a selective laser sintering process under specific parameters is known from EP 1021997, for example.

In addition to such a selective laser sintering or selective laser melting process (SLS, SLM) for metal powder that is particularly suitable for dental prostheses, other generative production processes may be suitable for other products, for example processes in which a granulate or some other solid material is sintered or melted by a high-energy beam of radiation, such as a laser beam or electron beam, and joined and cured thereby, or processes in which a plastic in solid or fluid form is selectively cured by photopolymerization by a high-energy beam of radiation, such as a laser beam or a concentrated light beam.

These generative production processes generally operate in such a way that successive layers of the curable material are applied to a substrate plate, for example by the substrate plate being successively and discontinuously lowered into a liquid bath of the curable material or by successive layers being applied one above the other by means of a powder application apparatus. After each layer application operation, certain parts of the layer are selectively cured and the product is built up layer by layer in this manner. After the product has been finished by curing the final layer, any regions of the material that have not been cured can be removed and in many cases can be re-used. The basic principle of the SLS or SLM process is described in EP 0734842 A1, the entire disclosure in which in this regard is incorporated herein.

One basic problem of generative production processes is the length of time that it takes between preparing the production data and finishing the product. Constructing a plurality of products simultaneously and generatively on a substrate plate in order in this way to increase the number of products made in a specific period of time is known from the prior art. This approach is appropriate, in particular, for products with very small dimensions relative to the dimensions of the substrate plate and results in an effective increase in productivity.

Reducing the downtime of a production apparatus by using a substrate plate which is detachably joined to a carrier, as a result of which the substrate plate can be removed immediately after finishing the products on that substrate plate and the substrate plate can be replaced with a new one in order to start a new production process, is known from EP 0734842 A1. Although this configuration makes it possible for the time needed to remove the products from the substrate plate not to be added to the downtime of the production apparatus, the apparatus still has the disadvantage that the production process cannot be started until the production data for all the products which are to be produced on a substrate plate are available and that the total time needed to make a product cannot be decisively reduced as a result, particularly when many small products are individually produced.

An apparatus which follows the same basic concept and which provides a conveying means within the production apparatus, with which one or a plurality of construction containers as well as metering containers or reservoirs can be conveyed in order to achieve simple, fast and reliable powder handling inside the production apparatus is known from WO 2008/128502. With that apparatus, it is possible to make products quickly in a construction container using a powder material and after finishing these products to make products from a different powder material in a second construction container. However, when using this production apparatus, the production process still takes at least as long as the time that elapses between generating the production data for all the products on the substrate plate and finishing the products, so production still takes a relatively long time with regard to each single product in a plurality of products.

A process for generative production of three-dimensional objects layer by layer and in which a plurality of objects are produced simultaneously in two construction regions is known from WO 2004/014636. One layer is applied in one construction region and selective curing by means of radiation is performed in a different construction region. Four process chambers are provided, which may be in the form of single, spatially separate chambers, or as sub-regions of two double chambers or a quadruple chamber. A laser which can be connected via a switching unit to a respective one of the process chambers is also provided. A disadvantage of the described apparatus and the described process for generative production of products with this apparatus is that separate control of the application operation in each of the process chambers is required in order to achieve simultaneous production with alternating curing and layer application in the respective process chambers. Although the apparatus and the process are suitable for the complex special application involving a plurality of products being made with different starting materials in respectively different process chambers, the production process and the apparatus are complex not only in structure, but also to control, and for that reason can be further optimized with regard to its productivity and efficiency in producing large numbers of small products, and with regard to the time that elapses between finishing the production data for a product and finishing the product itself.

Whereas, with known production processes and apparatus, only individual products that occupy about the size of the substrate plate can be produced not only in a productive manner, but also with a total production time that is acceptable for each single product, in the case of products whose dimensions are much smaller than the substrate plate, the only way to ensure productivity is by making several products together on one substrate plate. However, the production time required for a single product cannot be reduced to a desirably small duration in this case, but is increased by the generation of production data for all the products to be produced on the substrate plate and by the subsequent simultaneous production of all the products.

Another problem in the generative production of small products, by which are meant products whose base area is smaller, in particular by at least one order of magnitude, than the surface of the substrate plate, is that in many fields of application with specific product geometries, generative production is performed on an individual order basis, as for example in the production of dental prostheses in dental laboratories. In the latter case, the individual orders typically do not arrive simultaneously at the user of the production apparatus, but offset in time from one other. In order to achieve a high level of productivity and capacity utilization of the equipment in that case, the user must combine several orders in order to produce the products in these combined orders simultaneously on one substrate plate. However, this causes a substantial delay between receipt of order and finishing the product, especially for the first order received. If, in contrast, the user wishes to meet each order in the shortest possible time and produce the respective individual product, he is compelled to carry out the production process on a substrate plate with just one or a few products, which results on the whole in low utilization of the production apparatus capacity and in low productivity.

One object of the invention is to develop the known production processes such that both a high level of productivity and a short production time for each single product is also achieved for products whose dimensions are small in relation to the substrate plate. Another aim of the invention is to provide a production process and a production apparatus which shorten the time elapsing between receipt of order for a small product to be individually produced and completion of the product, without adversely affecting the productivity of the production process or the production apparatus.

These objects are achieved, according to the invention, by the steps of providing a substrate plate which is which is subdivided into a first substrate plate segment and at least one further substrate plate segment that are detachably joined to each other or to a base support, producing a first product on the first substrate plate segment by applying successive layers of material onto the first substrate plate segment and selectively curing predetermined regions of each applied layer of material after it has been applied, producing at least one further product on the at least one further substrate plate segment by applying successive layers of material onto the further substrate plate segment and selectively curing predetermined regions of each applied layer of material after it has been applied.

The process according to the invention is distinguished by a substrate plate being provided on which a first and a further product can be generatively produced simultaneously in a first and a respective further substrate plate segment, and by those substrate plate segments being detachably joined to each other or to a base carrier. This allows a single substrate plate segment to be removed after the product built thereon has been finished, in order to detach the product from the substrate plate segment, while a further product on another substrate plate segment continues to be generatively produced.

More specifically, it is possible with the process according to the invention for the layers of material to be applied to the at least two substrate plate segments in such a way that at least one of the layers of material extends over both substrate plate segments. In that case, the process can be carried out in such a way that one respective layer of material is firstly applied to the at least two substrate plate segments and that this layer of material is selectively cured in the region above both substrate plate segments.

In particular, the substrate plate segments may co-operate with a single coating apparatus in such a way that one product is constructed in a first stage of production on one substrate plate segment, for example with an n-th layer above the substrate plate, and a different product in a different stage of production is constructed on a different substrate plate segment, for example with a m-th layer above the substrate plate, where m is not equal to n and the n-th and m-th layer are applied by the coating apparatus in one operation.

With the process according to the invention, a plurality of products can therefore be produced on one substrate plate with staggered starting times for production, the products being partially produced simultaneously and also detached from the substrate plate with time shifts. In this way, it is possible to charge the substrate plate to capacity with a plurality of products, with the aim of high productivity, yet simultaneously to avoid the starting time for production not coming until after all the production data have been generated for all of the products to be produced on the substrate plate. Instead, the starting time for production can be defined individually for each substrate plate segment, and an individual production finishing time can also be achieved accordingly for each substrate plate segment. In this way, the production time for an individual product is shortened decisively.

It should be understood, as a basic principle, that the substrate plate can be subdivided into two, three or more substrate plate segments. This subdivision must be understood as a real physical subdivision into single components that can be combined accordingly to form one substrate plate. Layers can essentially be applied to all the substrate plate segments with a single, common layer application apparatus, which is preferred due to the efficient production associated therewith. In certain applications, however, it may be advantageous to coat the substrate plate segments with material by means of separate layer application apparatus, and it should also be understood in this regard that, although production of the products on the different substrate plate segments is started and also finished with respective time offsets in the process according to the invention, simultaneous production on a plurality of substrate plate segments is preferably carried out with simultaneous application of layers on all the substrate plate segments and with subsequent selective curing of specific regions for generative production of products, in order to achieve high levels of productivity.

According to a first preferred embodiment, the substrate plate segments are provided adjacent each other in such a way that no material can pass between the substrate plate segments. More particularly, appropriate sealing between the individual substrate plate segments may be provided for this purpose, or the substrate plate segments are joined together in such a way that it is not possible for material to pass between the substrate plate segments.

It is further preferred that the substrate plate segments are embodied as segments of a continuous conveyor device. This configuration makes it possible for products to be produced continuously and generatively in a particularly efficient manner. The substrate plate segments may be attached to a continuous conveyor belt, for example, or connected to each other in such a way that they form such a continuous conveyor belt in the form of a link chain. In this case, the substrate plate segments can be moved successively along an upper run and a lower run, layer application and selective curing of layers being carried out during movement along the upper run. Non-cured, applied material is removed from the space between produced products, and products can likewise be removed from the region of the upper run, for example, by appropriate suction devices or mechanical separators. However, it is also possible in like manner to have non-cured material removed in the region of the lower run or when transferring from the upper run to the lower run, using the force of gravity, for example, and then to take off the finished products either along with a substrate plate segment or directly from the substrate plate segment in the region of the lower run.

It is further preferred that the substrate plate segments be embodied and arranged in such a way that the first product or a group of first products is constructed on a single substrate plate segment and the further product or group of further products is constructed on one or a plurality of substrate plate segments. With this configuration, one or a plurality of products can be produced on a single substrate plate segment in order in this way to produce small products within a very short production time with a high level of productivity. It is also possible to produce a single product on a plurality of substrate plate segments. This may be advantageous whenever larger products, i.e., products whose longitudinal extension or contact surface is larger than the surface of one substrate plate segment, are to be produced by the process according to the invention. It is still further provided that a group comprising several different products can be produced on two or more substrate plate segments. This may be required in the case of products that extend very far in only one specific direction. With the process according to the invention, it is possible, for example, to produce a product whose length extends over a plurality of substrate plate segments. If several such products are to be produced, then it is possible with this development of the invention to create a group of such products extending over a plurality of substrate plate segments and then to produce them.

It is still further preferred that, in a first production step, the material is applied in a semi-continuous process onto the substrate plate and selectively predetermined regions of a respectively applied layer are cured, and, in a second production step, fully cured products are removed semi-continuously. This way of producing allows high-quality, generative production in a first production step and at the same time the removal of finished products in a second production step that is spaced apart from the first production step, without having any adverse effects on such generative production. This can be achieved, more particularly, by disposing the substrate plate segments on a continuous conveyor belt, or by such a continuous conveyor belt being formed by the substrate plate segments, and conveying the substrate plate segments accordingly from the first to the second production step. With this configuration, it is possible to keep the first production step in a closed and controlled atmosphere, in particular an inert atmosphere, in order to adjust the boundary conditions required for generative production in accordance with specific methods, whereas in the second production step the products can be ejected, or the second production step contains a lock, or the products are ejected from the controlled atmosphere when transferring from the first to the second production step.

It is further preferred that a layer of material is applied above at least two, preferably a plurality of substrate plate segments in a first step, that the layer of material is selectively cured in a second step, and that the maximum distance between the first substrate plate segment and the layer applied thereon to produce the first product differs in at least one, preferably more, and more particularly in all steps of the process from the maximum distance between the further substrate plate segment and the layer applied thereon to produce the further product. It should be understood, with regard to this variant, that one stage of the process comprises the sequence of layer application and selective curing, and is therefore performed repeatedly, thus giving rise to successive stages of the process, with a first and a second step being successively performed in each respective stage, and that a layer of material is applied in one operation onto at least two, more particularly onto a plurality of or all of the substrate plate segments, and that these are then selectively cured to produce generatively a plurality of products on the respective plurality of substrate plate segments. According to the invention, the layer is applied to the substrate plate segments in such a way that the distance between the applied layer and the substrate plate segments is different for at least two, in particular for each substrate plate segment. It should be understood in this regard that this maximum distance is different during layer application, and also or only during selective curing. This distance may differ in just one of several successive stages of the process consisting of the sequence of applying a layer and selectively curing that layer, but in particular may differ in every stage of the process, i.e., in such a way, typically, that the sum of the applied layers above one substrate plate segment is different from the sum of the applied layers above a different substrate plate segment, for example, because joint application to both substrate plate segments did not begin until a point in time at which one layer or a plurality of layers had already been applied to one of the two substrate plate segments.

The process may be implemented in such a way, for example, that the substrate plate segments can be moved individually in respect of their height, so that although one layer is applied to all the substrate plate segments in a common plane, the distance between that layer and the substrate plate segments is different, nevertheless, for each substrate plate segment, or in that the layer application apparatus is vertically adjusted between the substrate plate segments during the application operation.

It is still further preferred that the process be developed by the steps of removing non-cured material disposed on the first substrate plate segment, but without removing material from a different substrate plate segment, and subsequently removing non-cured material disposed on the other substrate plate segment. For semi-continuous generative production according to the invention, it is particularly advantageous at the point of removal if non-cured material can be removed in such a way that an adjacent region is not affected as a result, and that the non-cured material remains in that adjacent region. During generative production, the non-cured material has a supporting function and serves to receive and support layers lying above it. As a rule, therefore, the non-cured material must not be removed before the product has been fully constructed and cured. However, the prevent the necessity of such a stipulation meaning that finished products first have to travel along an extended path for the purposes of process safety until they arrive at the removal point where the non-cured material is removed, it is advantageous when the material removal device can effect the removal of material without affecting the immediately adjacent substrate plate segment in the process. This permits fast and semi-continuous production and avoids having to provide a safety gap between the layer application apparatus and the material removal device.

It is further preferred that, in a first phase of the production process, only such regions of a layer that are used to produce the first product are selectively cured, and in a last phase of the production process only such regions of a layer that are used to produce the further product are selectively cured, and that such regions of a layer that are used to produce the first and the further product are preferably cured in a middle phase of the production process between the first and the last phase. With the semi-continuous and simultaneous production of products in different stages of production thus achieved, a productive and fast process for individual production of small products by means of generative production processes is achieved.

According to another preferred embodiment, a separating wall which separates the construction space above each substrate plate segment from the construction space above an adjacent substrate plate segment is provided between the substrate plate segments. Such a separating wall allows or simplifies the removal of non-cured material above a substrate plate segment, without affecting the non-cured material in an substrate plate segment adjacent thereto. It should be understood in this regard that such a separating wall can be provided as part of the production apparatus and in such a case can be embodied, for example, in such a way that it is guided successively, and simultaneously with layer application, so that it has exactly the same height as the upper layer surface of the material applied in the region between two substrate plate segments, or somewhat less than that exact height.

In this respect, the separating wall may be produced during the product production process by curing the applied material. With this development of the invention, such a separating wall is produced from the applied material at the edge of a respective substrate plate segment during the production process. This approach has the advantage that structurally complex guidance systems for the separating wall can be dispensed with. Instead, a respective separating wall which can grow accordingly higher with each applied layer and which is successively guided to the overall height of the bed of layered material is constructed along the edge region of a substrate plate segment. The separating wall may then be removed when removing the products from the substrate plate segment, or in the course of removing non-cured material from the adjacent substrate plate segment.

The two aforementioned embodiments may be further developed by the separating wall being joined between two substrate plate segments to at least one of the two substrate plate segments. By joining the separating wall separating the two substrate plate segments to both the substrate plate segments, the substrate plate segments can also be securely sealed at the same time against any material passing through between them. The join can be effected by generative construction of the separating wall on one or on both the substrate plate segments, or by joining a component of the separating wall that belongs to the apparatus in an constructionally appropriate manner.

According to another preferred embodiment, each substrate plate segment is moved individually in relation to the layer application apparatus in such a way that the perpendicular distance between the surface of the substrate plate and layer applied by means of a layer application apparatus is altered and the resultant height of the bed of material on one substrate plate segment differs from the height of the bed of material on a different substrate plate segment. According to this embodiment, the height of each substrate plate segment can be individually adjusted, for example by means of an actuator that acts alternately on the substrate plate segments, or by means of a plurality of actuators, each of which is provided for a respective substrate plate segment. The substrate plate segments can thus be placed at different heights so that a layer of material can subsequently be applied in a plane above the substrate plate segments. This layer of material then lies at individually differing distances to the respective substrate plate segments, this is to say, at individual distances from the surface plane of the substrate plate segments on which the first layer of material was applied to the respective substrate plate segment. This embodiment is suitable for generative production of one product on a first substrate plate segment in a first stage of the process and a different product on a different substrate plate segment in a different stage of production, with common application of layers onto both substrate plate segments, and can be applied to a respective plurality of substrate plate segments with a respective plurality of products in different stages of the process.

It is also preferred that, before each application of material, the surfaces of the cured regions of the previously applied layer are polished. By such surface treatment, which may specifically be carried out as polishing, or by other machining processes with geometrically defined or geometrically undefined cutting, the geometrical precision of the generative production process is further increased. In particular, such machining provides a defined contact surface and joining point for the layer thereabove and the regions therein to be cured. As a result of this machining, a defined layer thickness is set, which is advantageous with regard to the geometric reproducibility of a finished product.

It is still further preferred that a single radiation source, in particular a single beam path from a single radiation source, is used to cure the first and the at least one further products, in particular all the further products. It should be understood, as a basic principle, that recourse can be made to a plurality of radiation sources or to a plurality of beam paths from a single radiation source in order to accelerate the production process. However, the production process according to the invention is distinguished in particular by a plurality of products being produced simultaneously and by these products being in different stages of production, i.e., being constructed from different numbers of layers, yet the special aspect is that not only can a layer be applied by a single layer application apparatus for all the substrate plate segments and for products to be made by constructing them thereon, but also that the curing of the specific regions of a layer can be carried out by a single radiation source for all the products to be produced.

According to another preferred embodiment, each substrate plate segment is raised and lowered in a vertical direction during the production process by means of a lifting device, and the substrate plate segments are lifted and lowered independently of each other. This independent lifting and lowering may be effected, in particular, by a respective actuator acting on a plurality of substrate plate segments, or by one respective actuator assigned to each respective substrate plate segment.

It is still further preferred that a plurality of substrate plate segments be coated with material in one operation by a single apparatus for applying material. This development of the invention makes an efficiently operating layer application apparatus possible, while at the same time allowing production of the respective products to be produced on the respective plurality of substrate plate segments to proceed individually.

The process may be developed, finally, by the steps of applying an n-th layer of material to a substrate carrier plate, selective curing of parts of the layer of material by directing high-energy radiation, in particular laser radiation, onto these parts of the layer of material, guiding the high-energy radiation over the n-th layer of material in accordance with guidance data which were calculated from the geometric data of an x-th cross-sectional plane of a first product, applying an n+1th layer of material onto the n-th layer of material, guiding the high-energy radiation over the n+1th layer of material in accordance with guidance data which were calculated from the geometric data of an x+1-th cross-sectional plane of the first product, guiding the high-energy radiation over the n-th layer of material in accordance with guidance data which were calculated from the geometric data of y-th cross-sectional plane of a second product, and guiding the high-energy radiation over the n+1th layer of material in accordance with guidance data which were calculated from the geometric data of a y+1-th cross-sectional plane of the second product, where x is not equal to y. With this development of the invention, at least two products are produced by subjecting them to selective curing in a commonly applied layer in two different regions of one and the same layer, wherein different heights in relation to the substrate plate are represented in that layer in the products themselves.

Another aspect of the invention is an apparatus for producing products having a specific geometry, comprising a substrate plate, a material application apparatus for applying material above the substrate plate, a radiation source for a high-energy beam of radiation, a beam guidance means for guiding the beam onto predetermined regions of a layer of material applied to the substrate plate, which according to the invention is developed by the substrate plate being subdivided into a plurality of substrate plate segments which are detachably joined to each other or to a base carrier.

The apparatus according to the invention is distinguished by a material application apparatus being disposed above a substrate plate, with which apparatus a layer of material can be applied to all the substrate plate segments of the substrate plate in one operation. A radiation source is also provided above the substrate plate. The apparatus for applying material and the radiation source are driven by means of a production control unit in such a way that the layer of material applied in the first operation can be selectively cured by the radiation source in a further operation, and is subdivided into a plurality of segments. The segments may be detachably joined to each other, by which is meant that each respective segment is joined to only one adjacent segment or that any segment can be joined to a plurality of surrounding segments. Alternatively, it is also provided that the segments be arranged adjacent each other and that each segment is detachably joined to a base carrier. With the apparatus according to the invention, it is possible in this way to produce generatively a plurality of products which are distributed on a plurality of substrate plate segments and to move the substrate plate segments in such a way with respect to their height relative to each other that the products are produced in different stages of production on the different substrate plate segments, and to remove an detach the product or products which has/have been produced on a first substrate plate segment before one or a plurality of products is/are removed and detached from a different substrate plate segment.

The apparatus according to the invention can be developed by adapting the material application apparatus to apply a layer of material simultaneously above a number of the plurality of substrate plate segments in one operation.

The inventive apparatus can also be developed such that the substrate plate segments and the material feeding device can be moved individually relatively to each other by means of one or a plurality of actuators in such a way that the distance between the surface plane of a first substrate plate segment and a region of the material layer applied thereon to produce a first product differs from the distance between the surface plane of a further substrate plate segment and a region of the same material layer applied thereon to produce the further product.

The apparatus according to the invention can be developed still further by providing by a material removal device, in particular a suction device for removing material, wherein the material removal device is adapted to remove uncured material from a region surrounding a finished product and is disposed in such a way that it can remove the material on a first substrate plate segment while leaving in place the material on a further substrate plate segment adjacent thereto.

According to another preferred embodiment, the apparatus according to the invention includes a controller for actuating the guide device for the high-energy beam of radiation, said controller being adapted to actuate the guide device in such a way that, in a first phase of the production process, only such regions of a layer that are used to produce the first product are selectively cured, and in a last phase of the production process only such regions of a layer that are used to produce the further product are selectively cured, and that such regions of a layer that are used to produce the first and the further product are preferably cured in a middle phase of the production process between the first and the last phase.

The apparatus according to the invention can be further developed by a controller for controlling the material application apparatus and/or for controlling at least one actuator for relative movement between the substrate plate segments and the material application apparatus, the controller being adapted so that the height of the bed of material on one substrate plate segment to be set after applying all the layers of material is set differently from the height of the bed of material on a different substrate plate segment. By this means, products with differing overall height can be produced on different substrate plate segments, and produced simultaneously.

It is further preferred that a treatment device for removing part of the surface of the cured regions of the material is disposed on the material application apparatus, preferably for grinding the surface of the cured regions of a previously applied layer of material.

It is still further envisaged that the substrate plate segments be disposed on a continuous conveyor belt which runs wholly or partially inside a process chamber which is sealed against the surroundings to such an extent that a controlled atmosphere, in particular an inert atmosphere can be created therein.

The apparatus may be further developed by providing at least one lifting device which is or can be coupled to any substrate plate segment in order to raise or lower the respective substrate plate segment in a vertical direction during the production process independently of the other substrate plate segments.

The apparatus according to the invention can be further developed by providing a single radiation source which is used, in particular by means of a single beam path, for curing the products being produced on all the substrate plate segments.

The apparatus according to the invention can be developed by a separating wall which is disposed between the substrate plate segments and which separates the construction space above each substrate plate segment from the construction space above an adjacent substrate plate segment.

It is also preferable that the separating wall is joined between two substrate plate segments to at least one of the two substrate plate segments or sealed against that substrate plate segment in such a way that no material can pass through between separating wall and substrate plate segment.

According to another preferred embodiment, the apparatus is distinguished by a controller for controlling the guide device for the high-energy beam of radiation, said controller being configured to actuate the guide device in such a way that the separating wall is produced during the product production process by curing the applied material.

Finally, the apparatus according to the invention can be developed by a controller for controlling the guide device for the high-energy beam, the controller being configured to guide the high-energy radiation over the n-th layer of material according to guidance data which were calculated from the geometric data of an x-th cross-sectional plane of a first product in order to cure parts of the n-th layer of material by directing high-energy radiation onto them, to guide the high-energy radiation over an n+1th layer of material according to guidance data which were calculated from the geometric data of an x+1-th cross-sectional plane of the first product in order to cure parts of the n+1th layer of so material by directing high-energy radiation onto them, to guide the high-energy radiation over the n-th layer of material according to guidance data which were calculated from the geometric data of a y-th cross-sectional plane of a second product in order to cure parts of the n-th layer of material by directing high-energy radiation onto them, and to guide the high-energy radiation over the n+1th layer of material according to guidance data which were calculated from the geometric data of a y+1-th cross-sectional plane of the second product, in order to cure parts of the n+1th layer of material by directing high-energy radiation onto them, where x is not equal to y.

Figure 2:
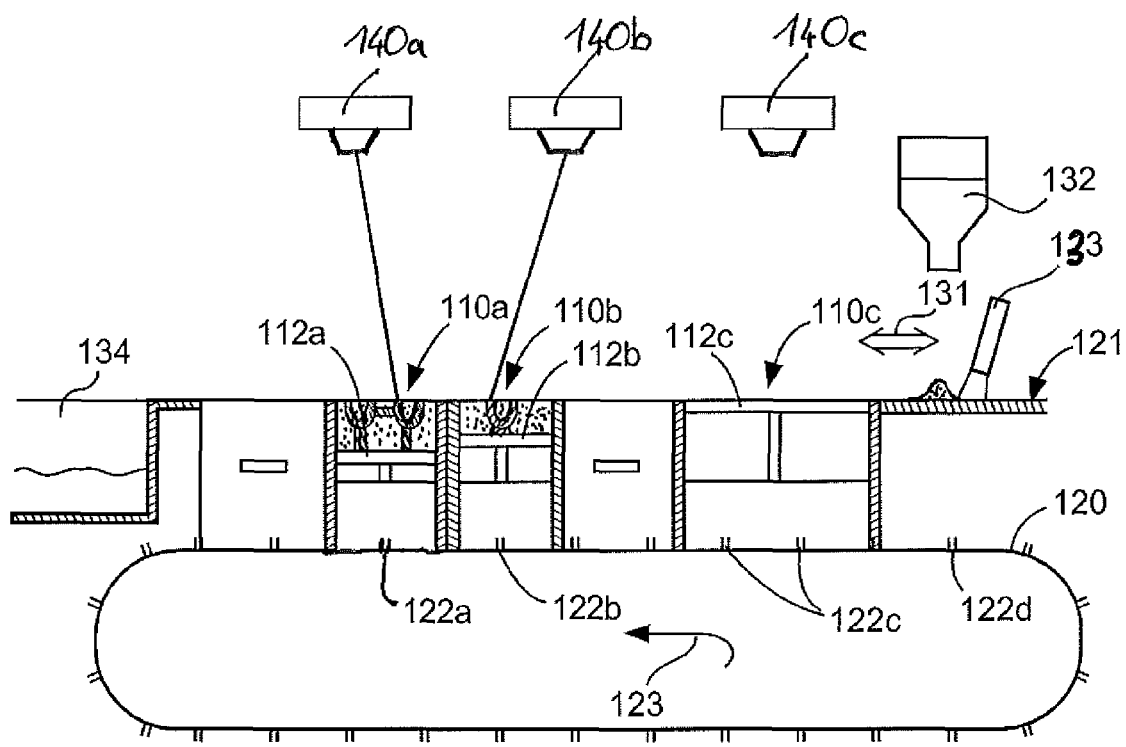
Figure 3:
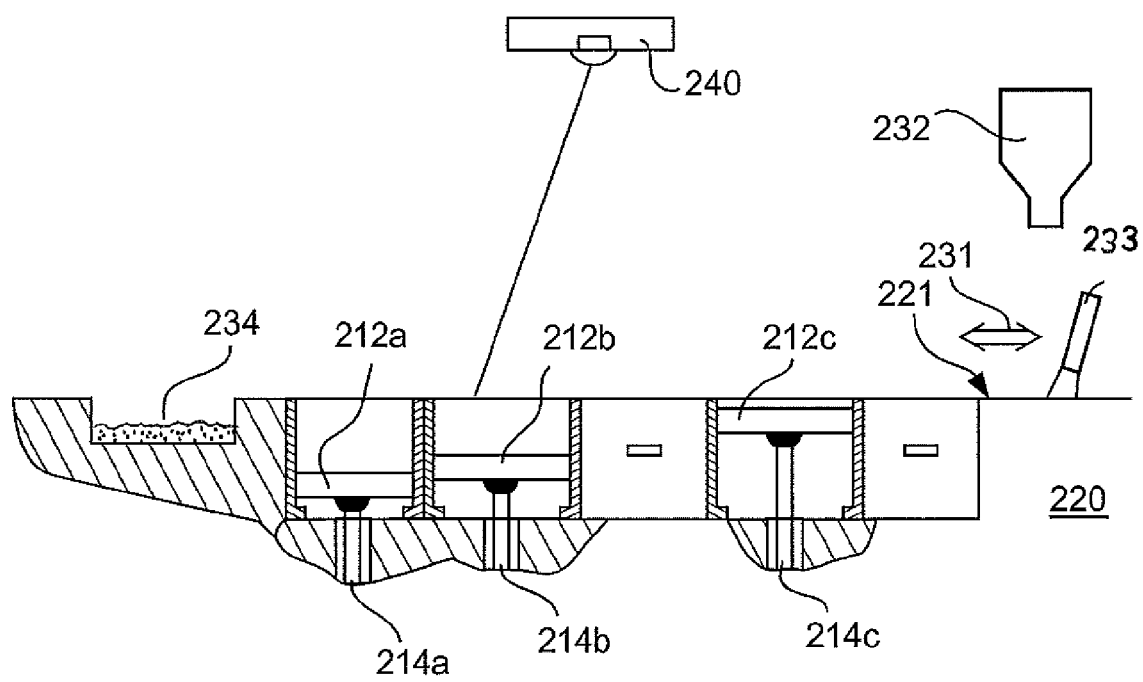
Figure 4:
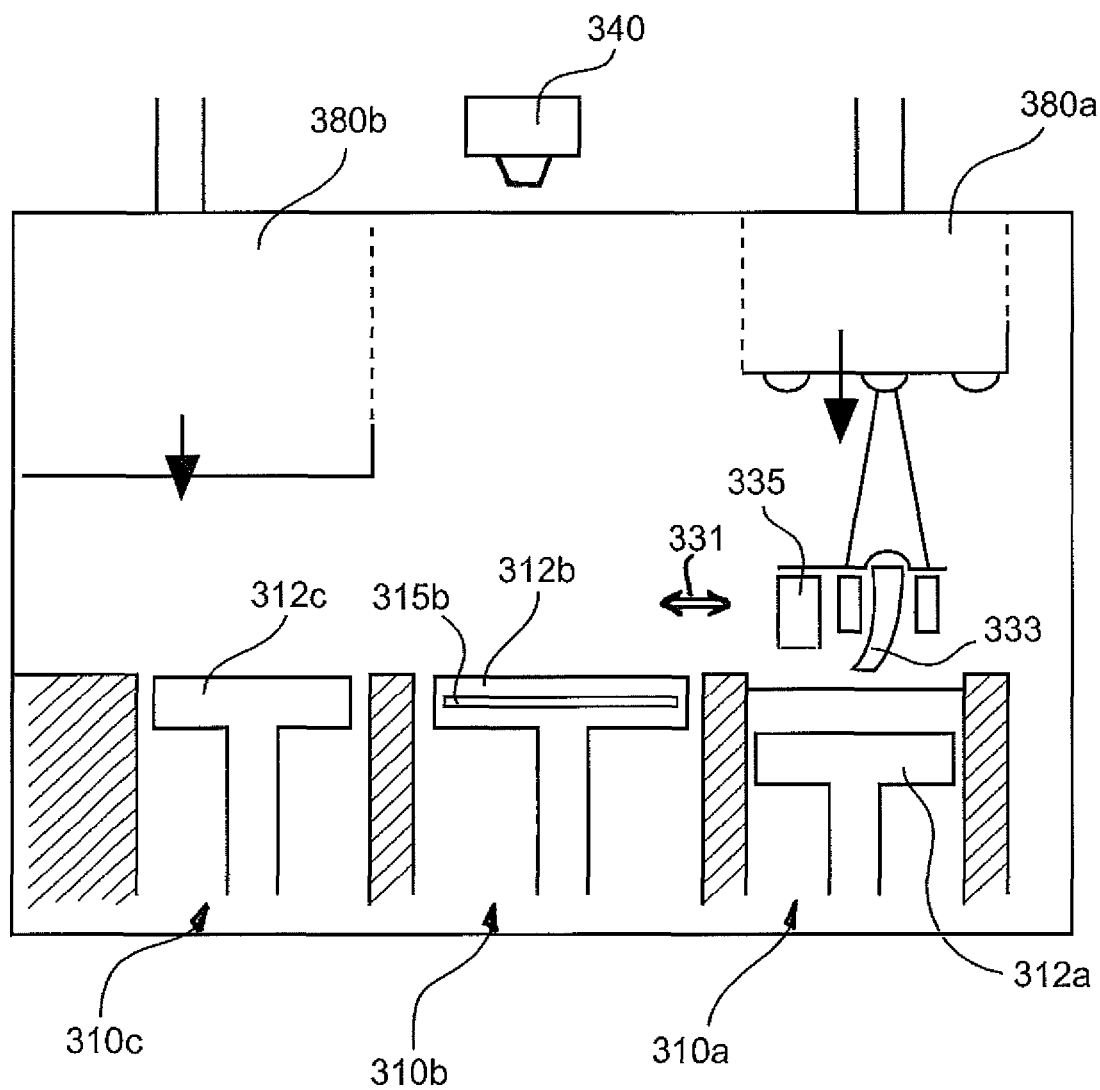
Figure 5:
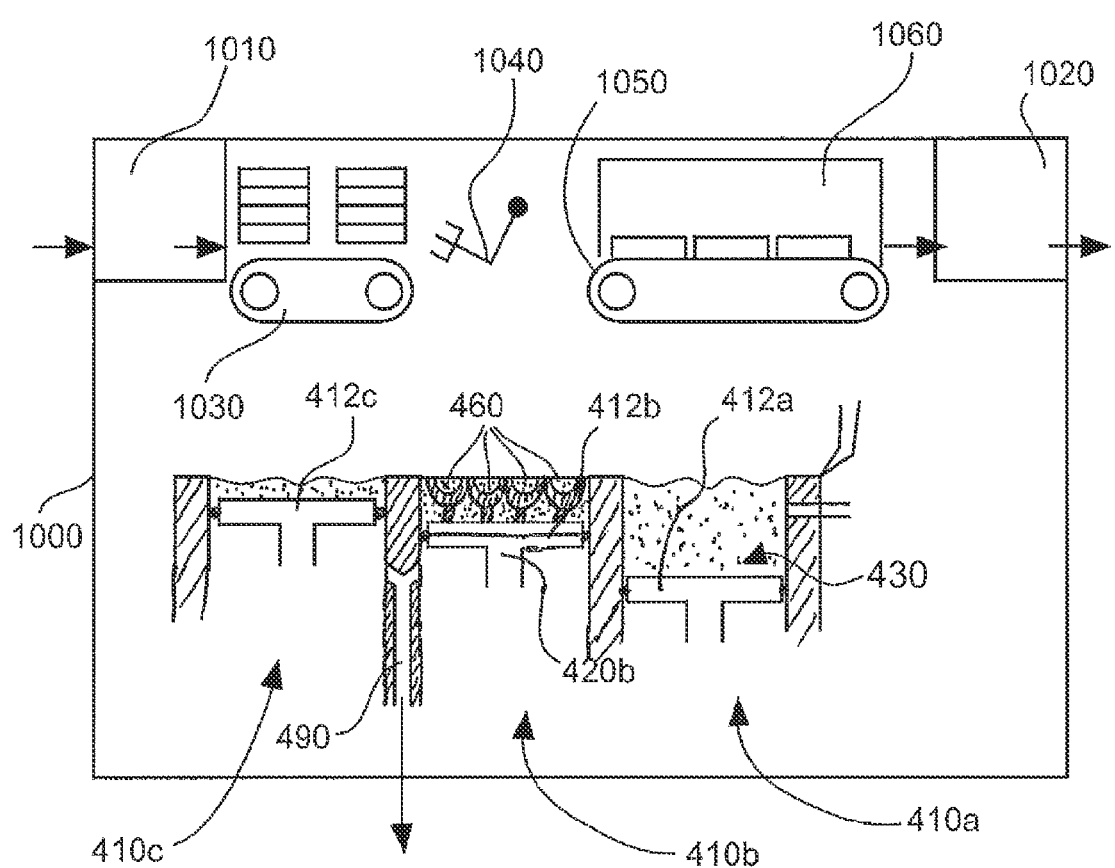
Figure 6:
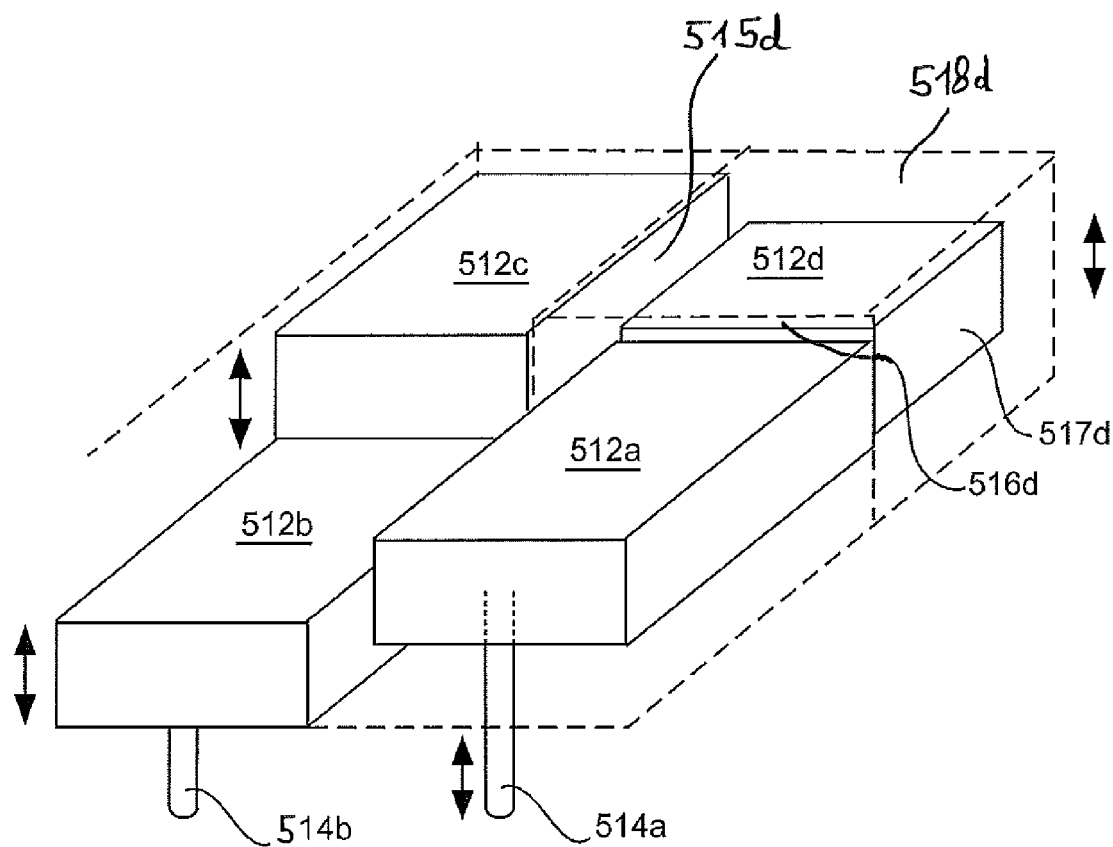
Figure 7:
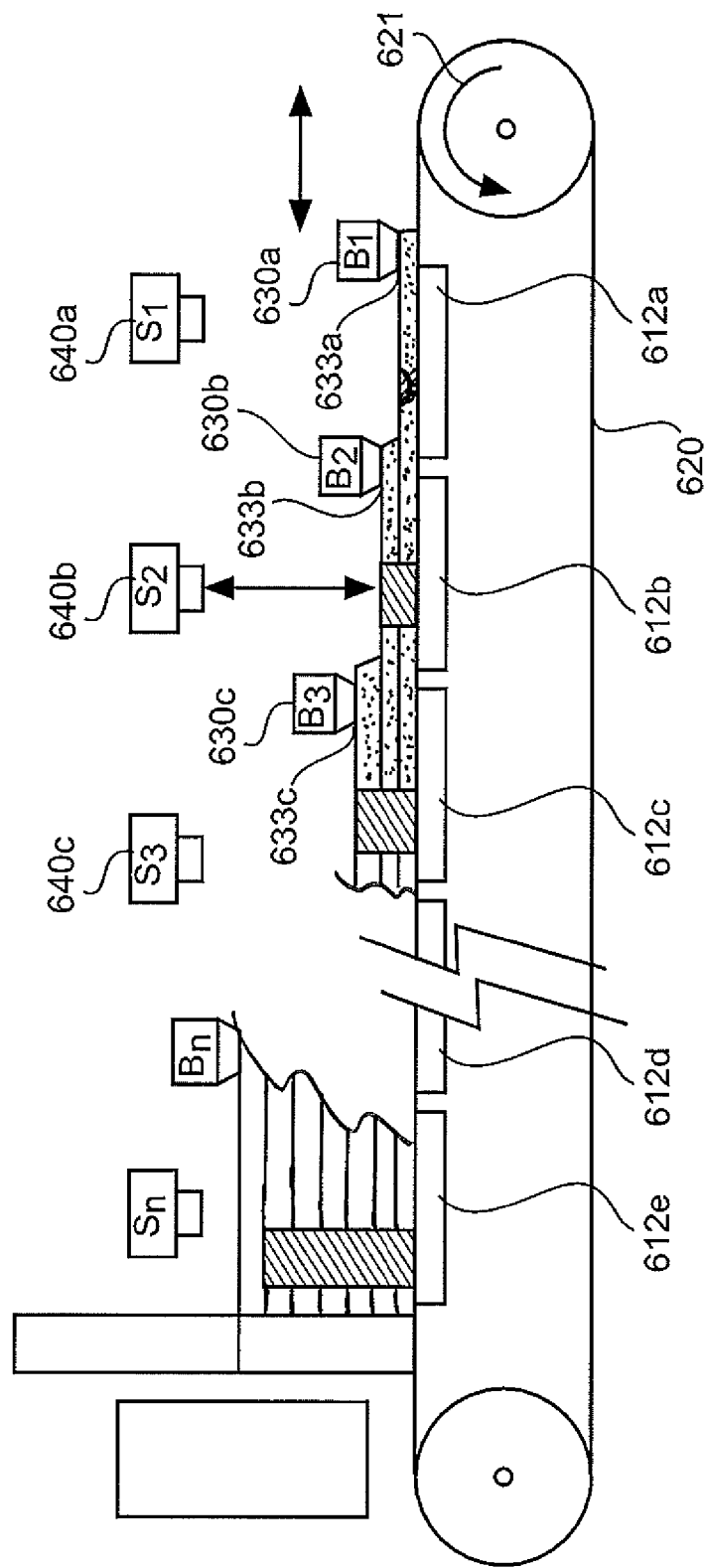
Figure 8:
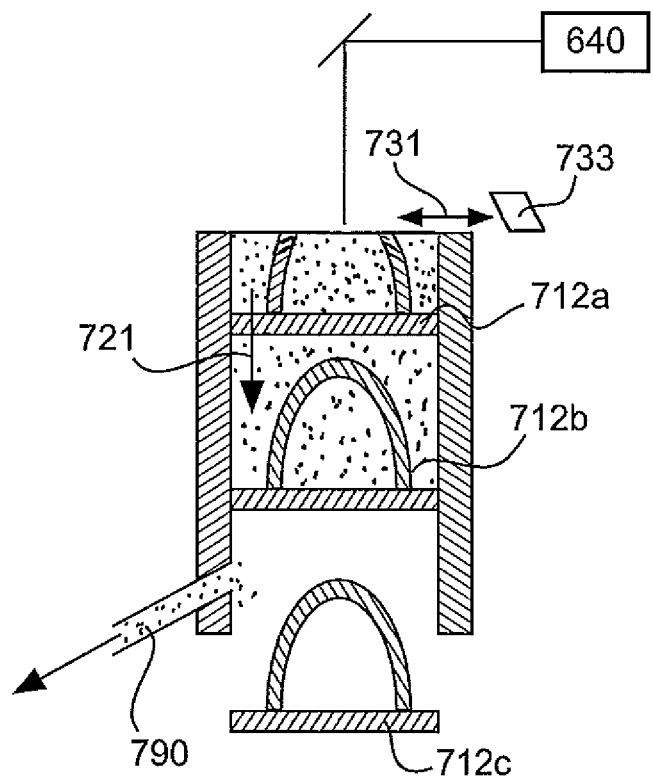

Some preferred embodiments of the invention shall now be described with reference to the attached Figures, in which:

FIG. 1A shows a schematic, longitudinal cross-sectional side view of a first embodiment of the invention, FIG. 1B shows a plan view of the embodiment in FIG. 1A, FIG. 2 shows a schematic, longitudinal cross-sectional side view of a second embodiment of the invention, FIG. 3 shows a schematic, longitudinal cross-sectional side view of a third embodiment of the invention, FIG. 4 shows a schematic, longitudinal cross-sectional side view of a fourth embodiment of the invention, FIG. 5 shows a schematic view of a production set-up according to a fifth embodiment of the invention, FIG. 6 shows a schematic view of a production set-up according to a six embodiment of the invention, FIG. 7 shows a schematic view of a production set-up according to a seventh embodiment of the invention, and FIG. 8 shows an eighth embodiment of the invention.

FIG. 1A shows a receiving device 20 for a total of eight inserts 10a-h arranged in two rows and four columns, as can be seen from FIG. 1B. Each insert 10a-h has an individually vertically adjustable substrate plate segment 12a-f. Each substrate plate segment 12a-f is individually vertically adjustable in a vertical direction 11 within its insert 10a-f. The vertical directions 11 for each of substrate plate segments 12a-f lie parallel to each other and perpendicular to the top surface 13a-f of substrate plate segments 12a-f, which is oriented horizontally, i.e., perpendicularly to the direction of gravity.

The recesses inside receiving device 20 are designed to each receive one insert 10a-f in which a substrate plate segment 12a-f is disposed. However, it should be understood that substrate plate segments which have a large base area than substrate plate 12a may also be inserted into receiving device 20, for example a base area that is twice as large or four times as large as the substrate plate segments shown in FIGS. 1a, b and which accordingly occupy two and four insert places, respectively.

A filling block 12g, 12h, which is not a substrate plate segment and which is not used for production, is inserted in inserts 10g and 10h.

Each substrate plate segment 12a-f can be vertically adjusted by means of an actuator 14a-f, which may be an electromotive linear actuator, for example. Actuator 14a-f is a component of insert 10a-f.

Each insert 10a-f is surrounded by a casing that is open at the top and rectangular in cross-section, more specifically square in cross-section, the casing having four wall as depicted, by way of example, by walls 15a-18a for insert 10a. Substrate plate segment 12a moves within these walls and seals itself at its lateral edge regions against the walls in such a way that coating material which is applied to the substrate plate segment cannot pass through between the substrate plate segment and the walls.

The upper end edges of the walls are flush with a surface 21 of receiving device 20 when inserts 10a-e are inserted into the receiving device. An upper surface of inserts 10g, h is flush in the same manner with surface 21 of receiving device 20.

A powder application apparatus 30 is provided, which comprises a powder transporter 32 from which powder can be dispensed on surface 21 of the receiving device, and which further comprises a slider 33 which can move along a direction of motion 31 reciprocally over surface 21 and substrate plate segments 12a-f and inserts 10a-h. Slider 33 distributes the powder dispensed from powder transporter 32 and applies a layer of powder above substrate plate segments 12a-f.

The powder application apparatus further comprises a collection unit 34 for surplus powder. Slider 33 pushes the powder which could not be applied as a powder layer above the substrate plate segments into collection unit 34.

As can be seen in FIG. 1A, substrate plate segments 12a-f are set to different heights by means of their actuators 14a-f, i.e., the distance between the top surface 13a-f of each substrate plate segment and surface plane 21 along which slider 33 moves and applies the powder like a blade, varies.

After each powder application, which is performed by moving slider 33 out of the right-hand position shown in FIG. 1A to a left-hand position, seen from here, in the region of catch tray 34, the layer applied during this powder application process above each substrate plate segment 12a-f is cured in predetermined regions by means of a radiation source, in this case a high-powered laser 40. This selective curing is carried out on the basis of control data corresponding to the cross-section of a product in the respective applied layer. With this selective curing process, the cured regions are joined at the same time to respective subjacent regions of the product that were previously cured. The curing process can be carried out, in particular, as selective laser sintering or selective laser melting (SLM). However, other curing techniques can also be applied to the principle of the invention, such as photopolymerization, for example. The beam of high-powered laser 40 is deflected thereby by beam deflection means in such a way that it hits the predetermined regions of the respective, previously applied layer and selectively cures these regions above all the previously coated substrate plate segments.

For that purpose, the beam deflection means is in signal communication with a controller. Production data for at least those products that are being simultaneously produced are stored in the controller. The production data specifically include positional data characterizing the position of a respective products on the substrate plate and geometric data characterizing the geometry of the respective product. The geometry data are prepared in such a way that they contain the geometrical data of individual cross-sections of the product. The respective position of such a cross-section and the geometry data stored for that cross-section geometry data correspond to the position of the respectively applied layer of material from which this product cross-section is produced, and to the geometry of that product in that layer of material. In the embodiment shown, with products perpendicularly upright on the plate, the geometrical data therefore correspond to horizontally extending cross-sectional planes through that product.

After the selected regions have been cured, slider 33 returns from the left-hand position into the right-hand position indicated in FIG. 1A. The surface of the selectively cured regions are ground by means of a grinding device disposed on the slider, in order to obtain a defined surface for the subsequent coating and curing process and a higher degree of geometrical precision of the generatively produced component.

After that operation, substrate plate segments 12a-f are lowered by a predefined distance corresponding to the thickness of the next layer to be applied. Due to this lowering, the surface of the previously applied layer and the selectively cured regions therein are no longer flush with surface 21 along which slider 33 moves with a lower spreading blade edge, but are below the plane of that surface 21 by the distance by which the substrate plate segment was lowered. A dosed amount of powder is then dispensed from powder transporter 32 onto surface 21, and that powder is applied as a layer above that lowered substrate plate segment by moving slider 33 to the left.

This operation is repeated until a product has been finished inside the powder bed applied layer by layer in this manner above a substrate plate segment. As can be seen from FIG. 1A, the time needed to finish one or a plurality of products above a substrate plate segment is different in the various inserts 10a-f; in the example shown, the product or products on substrate plate segment 12e in insert 10e are typically finished before the product or products on substrate plate segment 12c in insert 10c, if the products produced therein are of approximately the same height. Insert 10a is shown with substrate plate segment 12a raised to the position with maximum height, corresponding to the commencement of production.

After the products on a single insert 10a-f have been finished, this insert can be removed from receiving device 20 and replaced with a new insert whose substrate plate is in the topmost position. The products in the removed insert can be detached from the substrate plate after non-cured powder material has been removed. New products can be produced simultaneously on the newly inserted segment. With the time-shifted yet simultaneous construction of products in the apparatus made possible in this way, a high level of productivity in the generative production of products is achieved.

FIG. 2 shows a second embodiment of the invention, in which a plurality of substrate plate segments 112a-c can be coupled together as modules 110a-c on a continuous conveyor belt 120. A plurality of coupling points 122a, b, c, d are provided on conveyor belt 120, which simultaneously serve to fix a module 110a-c and to provide the power supply for an actuator 114a-c disposed in the module.

The actuator within each module is configured to adjust the height of substrate plate segments 112a-c individually in each case.

As can be seen in FIG. 2, substrate plate segments 112a and 112b are in the form of single segments, whereas substrate plate segment 112c is in the form of a double segment and extends twice the length along conveyor belt 120.

Like the inserts in FIGS. 1A, B, each module 110a-c is provided for its part with side walls within which substrate plate segments 112a-c can move vertically, and sealingly at the edges. The walls at the edges are flush at their top edges with a surface 121 on which powder can be dispensed from a powder transporter 132. Surface 121 lies horizontal, i.e., perpendicular to the direction of gravity, and by moving a slider 133 having a lower spreading blade edge which rests on surface 121 in a direction 131, the applied powder is distributed over substrate plate segments 112a-c and, after moving the slider from the right-hand position shown in FIG. 2 to a position to the left thereof, any surplus powder is pushed into a collecting container 134.

In the embodiment shown in FIG. 2, a powder bed of differing height is placed in each single module 110a-c, again by lowering substrate plate segments 112a-c individually and step by step, thus obtaining different production progress in each case, i.e., the layer applied in one operation by slider 133 is at a distance from the top surface of substrate plate segment 112c that differs from the distance from the surface of substrate plate segment 112b, which differs in turn from the distance to the surface substrate plate segment 112a. In this way, it is possible to generatively produce products with different production progress or in different stages of production in the individual modules, as can be seen from product 160, 161a which is shortly before completion in module 110a, and from product 160b which is about half finished in module 110b.

It is envisaged that the production set-up according to FIG. 2 functions in such a way that production in modules 110a-c progresses from the right to the left in the direction of conveyor belt 120, as shown by arrow 123. As soon as products in a production module have been finished, the conveyor belt is moved so far that that module can be removed, or the module is removed and the conveyor belt is advanced by the respective length of the module. In that case, a new module can be inserted on the right-hand side adjacent the position of slider 133 as shown, and generative production in this module can be started. In a further of production step, the removed module can be further processed. More particularly, the non-cured powder material can be removed from it, and the products produced therein can be removed from the substrate plate segment. The special advantage is that it is now possible, in the finished substrate plate segment which was previously subjected to simultaneous production with the other substrate plate segments, to remove the non-cured powder and the finished products without having to remove the powder from other substrate plate segments or having to stop the production process in the other substrate plate segments.

FIG. 3 shows a further embodiment of the invention. A plurality of substrate plate segments 212a-c are disposed adjacent each other in a manner identical to those in the embodiments in FIGS. 1A, B and 2, and are each surrounded by side walls sealingly at the edge areas of each substrate plate segment. The side walls are flush at their top edges with a surface 221 along which a slider 233 of a powder application apparatus moves in a direction 231, with its bottom edge serving as a spreading blade edge. In doing so, slider 233 applies a layer of powder above substrate plate segments 212a-c in one working stroke and pushes surplus powder into a collecting tray 234.

A laser beam source 240 used for selectively curing predetermined regions of the applied powder layer above each substrate plate segment is also provided. A controller for the production apparatus is provided which is configured in such a way that, after each layer application operation, predetermined regions above each substrate plate segment are cured by means of the laser beam source 240, as previously described.

In the embodiment according to FIG. 3, unlike in the embodiments shown in FIGS. 1A, B and 2, a respective actuator 214a-c which serves to adjust the height of substrate plate segments 212a-c individually and in that way to change individually the distance of the upper surface of the respective substrate plate segment from the plane in which the spreading blade edge of slider 133 moves is not a component of a module which is inserted into a receiving device. Instead, these actuators 214a-c are integrated into receiving device 220, and substrate plate segments 212a-c can be detachably coupled to actuators 214a-c.

Thus, with the embodiment shown in FIG. 3, it is possible in a similar manner to produce products semi-continuously by a generative production process such as SLS (Selective Laser Sintering) or SLM (Selective Laser Melting), in which products are simultaneously produced in a plurality of substrate plate segments and are in a different stage of production in each substrate plate segment. This is achieved by the substrate plate segments being individually adjustable in height, as a result of which it is possible to apply a powder bed above each substrate plate segment, the height of said powder bed differing from one substrate plate segments to the next, even though the new respective layers of the curable material are applied by means of a single slider 133 to the plurality of substrate plate segments 212a-c in a single operation.

FIG. 4 shows a fourth embodiment of the invention, which is distinguished by certain specific features. The embodiment shown in FIG. 4 is based on a basically similar principle to the embodiments shown in FIGS. 1A-3 and has a substrate plate segment 312a that may be disposed adjacent to other substrate plate segments (not shown) and which may be individually adjusted in its height. It should be understood that the principle described below with reference to FIG. 4 can be applied to the embodiments described in FIGS. 1A-3.

FIG. 4 shows a first dosing module 310a which serves as a dosing platform and which is filled with powder before a production process begins. A vertically adjustable base plate 312a is provided for this purpose at the lowermost position inside the dosing module. An emitter field 380 which pre-heats the powder filled into dosing module 310a is disposed above dosing module 310a.

A spreading blade 333 can be moved horizontally along a direction 331. A heater strip 335 which continuously heats the powder moved through the spreading blade and keeps it at the pre-heated temperature is disposed in front of blade 333 in the direction of motion.

Substrate plate segment 312b is disposed in a construction module 310b adjacent dosing module 310a. Substrate plate segment 312b can be moved vertically and individually within construction module 310a and independently of base plate 312a.

In relation to the direction of motion 331 of spreading blade 333, construction module 310b lies between the dosing module 310a and a collection module 310c which serves to receive any surplus powder that is pushed away by the spreading blade 333 over construction module 310b. Also disposed in collection module 310c is a base plate 312c which can be vertically moved individually and independently of base plate 312a and substrate plate segment 312b.

It should be understood, as a basic principle, that, instead of the single construction module 310b with substrate plate segment 312b, the embodiment shown in FIG. 4 may also comprise a plurality of such construction modules with substrate plate segments. This plurality of construction modules would be disposed adjacent each other in the direction of application 313, and the plurality of substrate plate segments would all be disposed between a dosing module 310a, disposed at one end in relation to the path of motion 331 of spreading knife 333, and a collection module 310c disposed at the other end.

Above collection module 310c there is also disposed an emitter field 380c which serves to keep the surplus material collected in the collection module at a desired temperature.

A heater 315b which keeps the substrate plate segment and the powder bed disposed thereon at a desired temperature is installed in substrate plate segment 312b.

The embodiment shown in FIG. 4 is optimized on a whole so that the powder is brought to a desired, pre-heated state prior to the selective curing process, by providing emitter fields 380a, b, heater strip 335 and heater 315b.

The production process which can be achieved with the embodiment shown in FIG. 4 comprises a sequence in which substrate plate segment 312b is firstly lowered by a specific amount which is equal to the thickness of the layer to be applied, and platform 312a of dosing module 315a is raised by a specific amount that is calculated from the cross-section of the platform and the volume of powder required for the next application.

This is followed by the pre-heated volume of powder being pushed out of the region of the dosing module by horizontal movement of spreading knife 333 over substrate plate segment 312b, in the process of which a layer is applied to the substrate plate segment 312b or to other substrate plate segments, where relevant. Surplus powder is brought into the collection module.

After application of this powder layer, the powder layer is selectively cured in predetermined regions by means of laser 340, and the regions cured thereby are joined to previously cured regions in subjacent layer.

Spreading blade 333 then returns and, by means of a grinding device which is disposed in front of the spreading blade in the direction of motion from left to right that is now traveled, the surface of the previously cured regions is lightly ground in order to improve the geometric fidelity of the generatively produced products and to strengthen the join with the regions to be subsequently cured. Alternatively to this configuration, in which the grinding operation is performed in a return stroke of the coating apparatus, it is possible to carry out the grinding operation jointly with the step of renewed powder application. In this case, the constructional arrangement of the grinding device on the coating apparatus must be selected such that the grinding device is located, in the direction of motion for powder application, before the position at which the powder is applied.

After spreading blade 333 has returned into its right-hand position as shown in FIG. 4, the process begins anew and is repeated until the product to be produced above substrate plate segment 312b or above some other substrate plate segment disposed in a row of substrate plate segments has been finished. The laser beam of laser beam source 340 is selectively guided thereby over every layer in such a way that previously computed regions of that layer, corresponding to the cross-section in the respective layer of the products to be produced on all the substrate plate segments, are selectively cured.

When the production process has been completed, the product can be separated from the substrate plate segment. It should be understood here, as a basic principle, that it is also possible to produce a plurality of products above one substrate plate segment and also that a plurality of substrate plate segments adjacent each other in different stages of production can be coated with the single spreading blade 333 and selectively cured with the single laser 340.

The powder collected in collection module 310c can be lifted by raising platform 312c and returned to the dosing insert by appropriate movements of spreading knife 333 from left to right, in order to start a new production processes and to re-use the powder thereby. Alternatively, it is also possible that the dosing module and the collection module now swap functions in the following production process, such that the layer application process is now performed by the spreading knife moving from left to right, and the grinding operation by a respectively reversed movement from right to left. In this case, the mobile unit comprising the heater strip, spreading blade and grinding device is preferably designed accordingly to be adjustable by 180° about a vertical axis.

FIG. 5 shows a further embodiment of the invention. The production set-up shown in FIG. 5 comprises a process chamber 1000 which has a first lock 1010 and a second lock 1020.

Substrate plate segments are fed through the first lock 1010 and laid onto a conveyor belt 1030. The substrate plate segments are stored intermediately on this conveyor belt and can be pre-heated, if necessary.

By means of a robot arm 1040, the substrate plate segments can be placed onto a construction platform 420*b* of a construction insert 410*b* in order to produce products generatively thereon. As previously described with regard to the embodiment according to. FIG. 4 and the three modules 312*a-c* shown therein, construction insert 410*b* is flanked by a dosing insert 410*a* and a collector insert 410*c*, and it should be understood that it is also possible to arrange a plurality of substrate plate segments adjacent each other between the dosing insert and the collector insert, in order to carry out semi-continuous production in the manner described in the foregoing.

In the embodiment shown in FIG. 5, substrate plate segment 412*b* can be moved to a lower position when the generatively produced products in the construction insert have been finished. In this lower position, the construction space above substrate plate segment 412*b* is connected to a powder suction duct 490, which is set into the side wall defining the construction space. The non-cured powder can then be sucked out of the region above substrate plate segment 412*b* via this powder suction duct 490.

Powder suction duct 490 is also designed in such a way that the powder which is pushed into the collector insert can be sucked out via suction duct 490, although it should be understood that this may or may not be provided as an optional additional function. Particular reference is made in this regard to the different operating modes of the embodiment with a dosing module and collection module, which were described in connection with the embodiment according to FIG. 4.

After the non-cured powder has been sucked out of the region above substrate plate segment 412*b*, the construction platform can be moved vertically into the uppermost position, and substrate plate segment 412*b* gripped, in turn, by means of robot arm 1040 and fed to a second conveyor belt 1050.

By means of the second conveyor belt 1050, substrate plate segment 412*b* along with the products disposed thereon are fed through a curing furnace 1060 in order to subject the products located thereon to curing and as a result to produce the product having the desired properties. After curing, substrate plate segment 412*b* can be passed through lock 1020 out of process chamber 1000.

With the set-up according to FIG. 5, it is possible not only to pre-heat and provide the plates, but also to carry out the entire generative production and powder 430 handling, as well as subsequent curing, in a controlled atmosphere, in particular in an inert gas or active gas atmosphere inside a process chamber 1000.

FIG. 6 shows a further aspect of the apparatus and process according to the invention. FIG. 6 shows four substrate plate segments 512*a-d* arranged in two rows and two columns. As can be seen, each of the substrate plate segments is individually vertically adjustable by means of a respective lifting/lowering device 514*a-d*. The substrate plate segments in a row as well as the substrate plate segments in a column can be moved vertically independently of each other, so products can be generatively produced in different stages of production on each of the substrate plate segments.

Separating walls are provided between the respective substrate plate segments for the purpose of individual creation of a powder bed above the respective substrate plate segment. In the embodiment shown here, these separating walls are not part of the apparatus, but are continuously constructed by selective curing of the powder material in the edge area of the respective substrate plate segments and therefore grow vertically with the generatively produced product in the middle region of the substrate plate segment. Alternatively, separating walls may be provided as parts of the production apparatus and disposed in such a way that their top edges are flush with a plane in which a spreading knife for powder application moves.

FIG. 7 shows a seventh embodiment of the invention. The embodiment includes a continuous conveyor belt 620, along which a plurality of substrate plate segments 612*a-e* are arranged in feeding direction 621.

Substrate plate segments 612*a-e* are placed in such a way that their upper surfaces lie in a common plane.

A plurality of coating apparatuses 630*a-d* are arranged above substrate plate segments 612*a-e*. The individual coating apparatuses 630*a-d* each comprise a spreading blade 633*a-d*. The bottom edge of spreading knife 633*a* is disposed at a distance of one layer from the surface of substrate plate segments 612*a-e*. Compared to the preceding spreading blade 633*a*, the bottom edge of spreading knife 633*b*, in contrast, is spaced apart from the surface of substrate plate segments 612*a-e* by one layer more, and the bottom edges of spreading blades 633*c, d* are raised accordingly by one layer thickness more in each case from the surface of the substrate plate segments, relative to the adjacent, preceding spreading blade.

The embodiment shown in FIG. 7 should basically be understood in such a way that a plurality of adjacently disposed individual coating apparatuses a, b, c, d . . . is provided in such a vertically staggered arrangement of heights.

Between each respective pair of layer application apparatuses 633*a, b, c* . . . there is a region in which the applied layer can be selectively cured by means of lasers 640*a, b, c, d*. Each individual coating apparatus is assigned thereby to a respective laser.

Conveyor belt 620 is advanced continuously or discontinuously during production in such a way that the upper run of the constellation shown in FIG. 7 moves from right to Left. As a result, a bed of material is applied by successive layers above substrate plate segments 612*a, b, c* . . . , which increases in height the further a substrate plate segment is conveyed from right to left by means of the conveyor belt The overall height of the generatively produced products on the respective substrate plate segments increases in the same, corresponding manner.

The principle of the embodiment shown in FIG. 7 must be understood in such a way that the desired height of the powder bed and thus of the products being produced can be achieved by a plurality of powder application apparatuses and the sum of the layers applied by means of these powder application apparatuses in one movement of the conveyor belt. Alternatively, conveyor belt 620 can also be moved reciprocally back and forth several times during one production process, and the plurality of powder application apparatuses or the conveyor belt can be vertically displaced thereby in order to apply a number of M×N powder layers powder layers, where M equals the number of reciprocal movements of the conveyor belt. It should be understood here that after each reciprocal movement of the conveyor belt, the N powder application apparatuses are raised by an amount or the conveyor belt is lowered by such an amount that equals N times the layer thickness, so that the powder application apparatus which is furthest to the right and which therefore lies lowest applies its layer in the next application operation to the layer that was previously applied by the powder application apparatus disposed furthest to the left and which therefore lies highest.

After the products have been produced accordingly, the non-cured powder material 590 is sucked out of the region above a substrate plate segment on which the finished constructed products lie, in the feeding direction leftwards of conveyor belt 520. It should be understood in this regard that powder is extracted only from above the substrate plate segment lying furthest to the left, whereas powder is not generally extracted from the substrate plate segment to the right thereof, due to the products there not being finished as yet. This can be achieved with separating walls that are constructed appropriately parallel between the substrate plate segments.

After the non-cured powder has been sucked out, the products produced on the substrate plate segment can be separated from the latter. After such separation, the surfaces of the substrate plate segment are made planar again, if necessary, by means of a device for surface smoothing disposed to the left of the suction process, in particular a milling or grinding station or an apparatus for laser smoothing, so that the substrate plate segment can subsequently be fed into a new generative production cycle.

It should be understood that the plurality of radiation sources may be provided by respective single laser sources or by a plurality of laser sources whose beam can be split and thus directed at a respective plurality of places. It should also be understood in this regard that the split beam and the plurality of beam paths thus generated can also be individually guided over the respective layers by respective beam guidance means in order to selectively cure each layer individually. According to the invention, the layer application process for all the substrate plate segments is performed in a first, common operation, followed by a selective curing process in a second operation. With an appropriate number of individual coating apparatuses, this can be carried out under continuous movement of the conveyor belt or—in the case of reciprocal movement of the conveyor belt—in a semi-continuous process.

A further embodiment of the invention can be seen in FIG. 8. In this embodiment, a plurality of substrate plate segments 712*a, b* are disposed one above the other, and the construction space above the respective substrate plate segments is bounded by common side walls 715-718. Substrate plate segments 712*a, b* . . . move in a vertical direction of motion from top to bottom through the construction space bounded by the side walls. In the respective construction space provided above the topmost substrate plate segment 712*b*, layers are iteratively applied by means of a layer application apparatus and selectively cured by means of a laser beam source. It should be understood in this regard that the layer application can be performed by means of a spreading knife in the same way as previously described. In the embodiment shown in FIG. 8, this spreading blade moves in a horizontal plane, that is to say, perpendicularly to the feeding direction of substrate plate segments 712*a, b*.

As soon as a sufficiently high bed of powder has been applied above a substrate plate segment and the product generatively produced and embedded therein has been finished, a new substrate plate segment may be placed thereon and is coupled accordingly to a conveying device for the vertical movement.

In a production section disposed underneath the layer application apparatus and the construction space in which generative production takes place, the substrate plate segments with finished products constructed thereon may be removed by sucking out the powder and separating the products from the substrate plate segment An extraction duct may be used for this purpose, as described with reference to FIG. 5, in order to convey the products subsequently into a region that is not bounded by side walls, thus allowing the products or the entire substrate plate segment to be removed from the vertical conveying device.

The invention claimed is:

1. A process for producing products having a specific geometry, the products including dental prostheses or auxiliary dental parts, the process comprising the steps of:
producing a plurality of products on the surface of a substrate plate by selective curing,
wherein a material is applied in successive layers,
selectively curing one or a plurality of predetermined regions by means of high-energy radiation and joining it or them to one or a plurality of regions of a subjacent layer after each application of a layer,
wherein said one or a plurality of predetermined regions are predetermined according to a cross-sectional geometry of the product in the respective layer,
characterized by the steps
providing a substrate plate which is subdivided into a first substrate plate segment and at least one further substrate plate segment that are detachably joined to each other or to a base carrier,
producing a first product on the first substrate plate segment by applying successive layers of material onto the first substrate plate segment and selectively curing predetermined regions of each applied layer of material after it has been applied,
producing at least one further product on the at least one further substrate plate segment by applying successive layers of material onto the further substrate plate segment and selectively curing predetermined regions of each applied layer of material after it has been applied, wherein each substrate plate segment is raised and lowered in a vertical direction during the production process by means of a lifting device, and that the substrate plate segments are lifted and lowered independently of each other.

2. The process according to claim 1, characterized in that a single radiation source is used to cure the first and the at least one further product.

3. The process according to claim 2, wherein a single beam path from the single radiation source is used to cure the first and the at least one further product.

4. The process according to claim 2, wherein the single radiation source is used to cure the first and all the further products.

5. The process according to claim 1, characterized in that the substrate plate segments are provided adjacent each other in such a way that no material can pass between the substrate plate segments.

6. The process according to claim 1, characterized in that the substrate plate segments are embodied as segments of a continuous conveyor device.

7. The process according to claim 1, characterized in that, in a first production step, the material is applied in a semi-continuous process onto the substrate plate and selectively predetermined regions of a respectively applied layer are cured, and, in a second production step, fully cured products are removed semi-continuously.

8. The process according to claim 1, characterized in that a separating wall is provided between the substrate plate segments, which separates a construction space above each substrate plate segment from the construction space above an adjacent substrate plate segment, and in that the separating wall is produced by curing the applied material during the process of producing the product.

9. The process according to claim 1, characterized in that before each application of material, the surfaces of the cured regions of the previously applied layer are polished.

10. The process according to claim 1, characterized in that a plurality of substrate plate segments are coated with material in one operation by a single apparatus for applying material.

11. The process according to claim 1, characterized in that the maximum distance between the first substrate plate segment and the layer portion applied thereon to produce the first product differs in all steps of the process from the maximum distance between the further substrate plate segment and the layer portion applied thereon to produce the further product.

12. The process of claim 1, wherein selective curing includes selective sintering or fusing.

13. The process according to claim 1, wherein the first product and the at least one further product are different products.

* * * * *